United States Patent [19]

Matsuoka et al.

[11] Patent Number: 5,965,764

[45] Date of Patent: Oct. 12, 1999

[54] PROCESS FOR PRODUCING A NITRILE

[75] Inventors: Shotaro Matsuoka; Masaaki Suematsu, both of Aichi; Mamoru Ishikawa, Shiga, all of Japan

[73] Assignee: Toray Industries, Inc., Japan

[21] Appl. No.: 09/128,939

[22] Filed: Aug. 5, 1998

[30] Foreign Application Priority Data

Aug. 6, 1997 [JP] Japan .................................. 9-212249

[51] Int. Cl.$^6$ ................................................. C07C 253/00
[52] U.S. Cl. ........................................... 558/311; 558/312
[58] Field of Search ...................................... 558/311, 312

[56] References Cited

U.S. PATENT DOCUMENTS 5,817,827 10/1998 Bonrath et al. ......................... 558/312

*Primary Examiner*—Johann Richter
*Assistant Examiner*—Joseph Murray
*Attorney, Agent, or Firm*—Austin R. Miller

[57] ABSTRACT

Process for producing a nitrile by dehydration reaction of an amide in the presence of a carboxylic acid having the same radical as the amide, or by adding urea to a carboxylic acid with the carboxylic acid either molten or dissolved in a solvent, where the amount of urea used is less than about 0.8 in molar ratio to the carboxylic acid, or when an exhaust gas distillate line connected to the reactor is kept at about 60° C. or higher, or while a gas that is inert to the reaction is fed into the reaction and the produced nitrile and water are concurrently distilled out.

13 Claims, No Drawings

PROCESS FOR PRODUCING A NITRILE

BACKGROUND OF THE INVENTION

The present invention relates to a safe, high yield process for producing a nitrile from an amide. This invention further relates to the particular reaction between urea and a carboxylic acid.

In more detail, the present invention relates to a process for producing a nitrile represented by the formula (II):

where R represents a substituted or non-substituted alkyl group, or an alkenyl group, or an alkynyl group, or an aryl group or an aralkyl group or a mixture thereof. The process comprises dehydration of an amide represented by the following formula (I):

where R is as defined above. The process is conducted in the presence of a carboxylic acid:

where R is as defined above.

The nitrites produced are very important compounds, useful as intermediate products in production of medicines, agricultural chemicals, dyes, pigments, etc.

PRIOR ART

Various nitrile production processes are known, and production processes using dehydration of an amide are generally discussed in JP-B-50-30607, JP-B-53-23819, JP-B-23820, JP-B-53-23821, JP-A-50-13326, JP-A-62-167749, JP-A-62-289552, JP-A-02-295957, for example.

Nitrile production processes using the reaction between a carboxylic acid and urea are also discussed in JP-B-62-5899, JP-A-54-95541, and Organic Synthesis Collective, Vol. 4, p. 513 (1963).

BRIEF SUMMARY OF THE INVENTION

However, these processes have encountered several important problems in industrial use. The dehydration reaction of an amide has the disadvantage that water is produced simultaneously, and causes hydrolysis with the raw amide or the nitrile product, to produce a carboxylic acid. This inhibits the yield of the intended nitrile.

Furthermore, in obtaining a nitrile from carboxylic acid and urea, the carboxylic acid and the urea are brought together in advance; that is, the carboxylic acid and the urea are physically present together in the reaction vessel before the start of the reaction. This is done in order to avoid the trouble of continuously adding urea, or in order to improve the carboxylic acid dissolution temperature. However, in such an operation where both the compounds coexist in the reaction zone, a sudden reaction ultimately occurs between the carboxylic acid and the urea, causing the reaction mixture to bump, or generating an exhaust gas of carbon dioxide, ammonia, etc. which is suddenly generated in a large burst. This inconveniences the processing, adversely affects safety and environment, and presents a serious obstacle to processability.

It can be considered to use an excessive amount of urea in comparison to the charged amount of carboxylic acid, in an attempt to almost perfectly consume the raw carboxylic acid and to increase the production of amide as an intermediate product, and furthermore for increasing the production of a nitrile from the subsequent dehydration reaction. However, in this case, the urea not used for the reaction self-decomposes to form a sublimate, thereby plugging the exhaust gas line connected to the reactor. This is harmful to both working convenience and safety.

Moreover, when a nitrile is obtained from the reaction between a carboxylic acid and urea, this causes water, carbon dioxide and ammonia to be produced simultaneously. They are discharged outside the system from the reactor through an exhaust gas distillate line. In this case, a sublimate such as ammonium bicarbonate, a decomposition product of urea itself, etc. is discharged simultaneously, and this plugs the exhaust gas line, and raises the internal pressure of the reactor. This is a problem threatening safety and requiring frequent and laborious unplugging work.

Furthermore, in the amide dehydration reaction, if byproduct water is distilled out of the reactor, the equilibrium shifts toward the product side, to ensure smooth progression of reaction. For more advantageous production of the nitrile, it is necessary to distill out the produced nitrile together with the byproduct water from the reactor. This further shifts the equilibrium toward the product side, and ensures smoother progress of the reaction. In this case, the nitrile can also be isolated without thermal deterioration. However, if, on the contrary, the nitrile and byproduct water are not smoothly distilled out of the reactor, the reaction rate becomes low. In addition, the nitrile retained in the reactor reacts with byproduct water, and is converted into the corresponding carboxylic acid. This decreases nitrile production seriously.

For the foregoing and other reasons these conventional nitrile production processes are not industrially satisfactory.

OBJECTS OF THE INVENTION

An object of the present invention is to provide a process for producing a nitrile at a high yield without any safety problem relating to the amide dehydration reaction or the reaction between urea and carboxylic acid.

Other objects of the present invention will be clarified in the following description.

BRIEF DESCRIPTION OF THE INVENTION

We have found surprisingly that if the dehydration reaction is effected in the presence of a carboxylic acid corresponding to the amide, byproduction of carboxylic acid is inhibited while the yield of the intended nitrile improves.

We have also found that if urea is added to the carboxylic acid when the carboxylic acid is melted or is substantially completely dissolved in a solvent, the corresponding nitrile can be produced stably without bumping of the reaction mixture caused by sudden reaction between the carboxylic acid and urea, or without sudden mass generation of exhaust gas of carbon dioxide, ammonia, etc.

We have also found that if the amount of urea used is controlled at less than about 0.8, expressed as molar ratio to the carboxylic acid, the nitrile can be stably produced without inconvenient plugging in the exhaust gas line.

We have also found that if the exhaust gas distillate line connected to the reactor is kept at about 60° C. or higher, almost nothing plugs the line, and that this solves the safety and working problems.

We have also found that if the produced nitrile is distilled out while an inert gas is fed into the reaction zone, the produced nitrile and byproduct water can be smoothly distilled out, and that the desired nitrile can be obtained at a high yield. The amide is represented by the following formula (I):

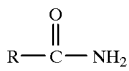 (I)

where R represents a substituted or non-substituted alkyl group, or an alkenyl group, or an alkynyl group, or an aryl group or an aralkyl group, or any mixture thereof. The product nitrile is represented by the following formula (II):

R—CN (II)

where R represents a substituted or non-substituted alkyl group, or an alkenyl group, or an alkynyl group, or an aryl group, or an aralkyl group, or any mixture thereof.

The dehydration reaction is effected in the presence of the carboxylic acid represented by following formula (III):

R—COOH (III)

where R represents a substituted or non-substituted alkyl group, or an alkenyl group, or an alkynyl group, or an aryl group or an aralkyl group, or any mixture thereof.

As a preferred embodiment the dehydration reaction is effected in the presence of the residue remaining after forming the nitrile represented by the formula (II).

Furthermore, in the preferred process for producing a nitrile of the present invention, the conversion percentage of the carboxylic acid represented by the formula (III) is less than 100%, and the dehydration reaction is effected while the carboxylic acid represented by the formula (III) remains in the produced amide. In such a case, it is preferable that urea is added to the carboxylic acid represented by the formula (III) when the carboxylic acid is in a molten condition, or that urea is added to the carboxylic acid represented by the formula (III) when the carboxylic acid is well dissolved in a solvent, and that the amount of urea used is less than about 0.8, expressed as a molar ratio, relative to the amount of the carboxylic acid.

Furthermore, in the present invention, it is preferable that the produced nitrile and water are distilled out while a gas that is inert to the dehydration reaction of the amide is fed in during the reaction. The inert gas may be any one of nitrogen, helium, argon or carbon dioxide. The "R" radicals in the compounds represented by the formulae (I), (II) and (III) are preferably aryl groups in this and other cases.

Furthermore, in the present invention, it is preferable that an inorganic acid and/or a cobalt salt is introduced as a catalyst, and that the exhaust gas distillate line connected to the reactor for discharging the byproducts of the reaction is kept at about 60° C. or higher.

DETAILED DESCRIPTION OF THE INVENTION

The present invention is described below in detail.

In the process for producing a nitrile by dehydration of an amide, the starting material is represented by the following formula (I):

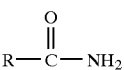 (I)

where R represents a substituted or non-substituted alkyl group, alkenyl group, alkynyl group, aryl group or aralkyl group. The designation "R" stands for a substituted or non-substituted alkyl group with 1 to 20 carbon atoms, or an alkenyl group, or an alkynyl group, or a substituted or non-substituted aryl group with 6 to 20 carbon atoms, or a substituted or non-substituted aralkyl group with 6 to 20 carbon atoms.

It is preferable to use an amide in which "R" of the formula (I) designates a substituted or non-substituted aryl group with 6 to 20 carbon atoms. Furthermore, an amide represented by the following formula (IV):

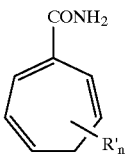 (IV)

where R' designates an alkyl group with 1 to 4 carbon atoms, an alkoxy group with 1 to 4 carbon atoms, or a halogen atom, and n is zero or an integer of 1 or 2, is preferred.

The amides which can be used include, for example, aliphatic amides such as acetic amide, valeric amide, caproic amide, lauric amide, stearic amide and oleic amide, aromatic amides such as benzamide, toluamide, ethylbenzamide, chlorobenzamide, dichlorobenzamide, bromobenzamide, dibromobenzamide, methoxybenzamide, ethoxybenzamide, dimethoxybenzamide, nitrobenzamide, cyanobenzamide, aminobenzamide, hydroxybenzamide, dihydroxybenzamide, hydroxymethylbenzamide, formylbenzamide, phthalamide and naphthoamide, etc.

These amides can be easily produced by a reaction between a carboxylic acid and ammonia, or between a carboxylic acid and urea or ammonium carbonate, etc. to produce ammonia under the reaction conditions, or by the reaction between a carboxylic acid halide and ammonia, etc. In the present invention, any of the amides obtained by the above methods can be used after being purified, or even as it is without being purified, without any problem.

The dehydration reaction of the amide in the present invention is carried out in the presence of a carboxylic acid represented by the following formula (III):

R—COOH (III)

where R stands for a substituted or non-substituted alkyl group, alkenyl group, alkynyl group, aryl group or aralkyl group. It is preferable that "R" stands for a substituted or non-substituted alkyl group with 1 to 20 carbon atoms, alkenyl group, alkynyl group, substituted or non-substituted aryl group with 6 to 20 carbon atoms, or substituted or non-substituted aralkyl group with 6 to 20 carbon atoms.

Specifically, the dehydration reaction of the amide is effected in the presence of an aliphatic carboxylic acid such as acetic acid, valeric acid, caproic acid, lauric acid, stearic acid or oleic acid, or an aromatic carboxylic acid such as benzoic acid, toluic acid, ethylbenzoic acid, chlorobenzoic acid, dichlorobenzoic acid, bromobenzoic acid, dibromobenzoic acid, anisic acid, ethoxybenzoic acid, dimethoxybenzoic acid, nitrobenzoic acid, cyanobenzoic acid, aminobenzoic acid, hydroxybenzoic acid, dihydroxybenzoic acid, hydroxymethylbenzoic acid, formylbenzoic acid, phthalic acid or naphthoic acid. These carboxylic acids can be easily produced by publicly known techniques such as vapor phase or liquid phase air oxidation, nitric acid oxidation, electrolytic oxidation or reagent oxidation.

In the present invention, the carboxylic acid can be supplied together with the raw material, or can be added during the reaction. Since the residue remaining after removing the nitrile obtained by the amidation reaction mainly contains byproduct carboxylic acid, it can be recycled. That is, the dehydration reaction of the amide can also be effected in the presence of the residue.

In the dehydration reaction of the amide in the present invention, the raw material may be an amide produced from a carboxylic acid according to known technique. In this case, the conversion percentage of the carboxylic acid is kept low, to leave the carboxylic acid in the produced amide, in order to use the reaction mixture, as it is, for the dehydration reaction. There are several techniques for making an amide from a carboxylic acid, as described before. An especially preferable method is to produce the amide by the reaction between a carboxylic acid and urea. In this case, the conversion percentage of the carboxylic acid should be less than about 100 mol %. A preferable range is about 50 to 99 mol %, and a more preferable range is about 60 to 95 mol %.

The amount of carboxylic acid used in the dehydration reaction of the present invention is about 1 to 50 wt. % based on the weight of the raw amide. A preferable range is about 5 to 30 wt. %.

The dehydration reaction of the present invention can also be effected in the presence of a catalyst such as an inorganic acid or cobalt salt. The inorganic acids which can be used include boric acid, phosphoric acid, phosphorous acid, sulfuric acid, etc. The cobalt salts which can be used include cobalt borate, cobalt acetate, cobalt oxide, cobalt chloride, cobalt sulfate, etc. A mixture of one or more of these compounds can be used. It is preferable to use cobalt borate or a mixture of boric acid and cobalt acetate.

It is preferable that the amount of the catalyst is about 0.01 to 30 wt. % based on the weight of the amide. A more preferable range is about 0.1 to 10 wt. %.

The temperature of the dehydration reaction of the present invention depends on the compounds used, but is usually about 200 to 400° C. A preferable range is about 220 to 300° C. The reaction can be effected at atmospheric pressure, with pressurization or under reduced pressure. It is preferable that the reaction is effected at atmospheric pressure or under reduced pressure. The reaction can be effected in vapor phase or liquid phase. The amide and the carboxylic acid can be melted and so used for the reaction, or can be dissolved in a solvent for the reaction. Even if the reaction is a batch or continuous reaction, no inconvenience is caused.

In the present invention, in the process for producing a nitrile by reaction between a carboxylic acid and urea, a carboxylic acid represented by the following formula (III):

R—COOH     (III)

where R stands for a substituted or non-substituted alkyl group, alkenyl group, alkynyl group, aryl group or aralkyl group, is used as a raw material. It is preferable that "R" stands for a substituted or non-substituted alkyl group with about 1 to 20 carbon atoms, alkenyl group, alkynyl group, substituted or non-substituted aryl group with about 6 to 20 carbon atoms or substituted or non-substituted aralkyl group with about 6 to 20 carbon atoms. Specifically, the carboxylic acids include aliphatic carboxylic acids such as lauric acid, stearic acid and oleic acid, aromatic carboxylic acids such as benzoic acid, toluic acid, ethylbenzoic acid, chlorobenzoic acid, dichlorobenzoic acid, bromobenzoic acid, dibromobenzoic acid, anisic acid, ethoxybenzoic acid, dimethoxybenzoic acid, nitrobenzoic acid, cyanobenzoic acid, aminobenzoic acid, hydroxybenzoic acid, dihydroxybenzoic acid, hydroxymethylbenzoic acid, formylbenzoic acid, phthalic acid and naphthoic acid, etc.

These carboxylic acids can be produced easily by known techniques such as vapor phase or liquid phase air oxidation, nitric acid oxidation, electrolytic oxidation or reagent oxidation. As the carboxylic acid used as the raw material, a product obtained by any of the above techniques can be used after it has been purified, or even as it is without being purified, without any problem. In the present invention, from the reaction between a carboxylic acid and urea, an amide represented by the following formula (I):

(I)

where R stands for a substituted or non-substituted alkyl group, alkenyl group, alkynyl group, aryl group or aralkyl group is at first produced, and in succession by the dehydration reaction of the amide, the intended nitrile can be produced. In this case, it is preferable that R stands for a substituted or non-substituted alkyl group with 1 to 20 carbon atoms, alkenyl group, alkynyl group, substituted or non-substituted aryl group with 6 to 20 carbon atoms or substituted or non-substituted aralkyl group with 6 to 20 carbon atoms.

The amide produced as an intermediate product can be isolated and purified to be used for the dehydration reaction, or the crude product can be used as it is. Usually, the crude product is directly used for the dehydration reaction.

In the reaction between a carboxylic acid and urea of the present invention, it is preferable that urea is added at a rate not causing sudden reaction with the carboxylic acid, to the carboxylic acid when the carboxylic acid is molten or perfectly dissolved in a solvent. Urea can be added as a solid or in a molten state or as a solution in a solvent that is inactive to the reaction.

As the solvent used in the reaction between a carboxylic acid and urea of the present invention, any solvent can be used without inconvenience if it is inactive to the reaction between urea and a carboxylic acid. The solvents which can be used include aromatic or aliphatic hydrocarbons such as cumene, trimethylbenzene, tetramethylbenzene, cymene, diisopropylbenzene, decalin, tetralin, methylnaphthalene, dimethylnaphthalene, isopropylnaphthalene and diisopropylnaphthalene, aromatic chlorides such as chlorotoluene, dichlorotoluene, dichlorobenzene and trichlorobenzene, aromatic nitro compounds such as nitrobenzene and nitrotoluene, aromatic ether compounds such as diphenyl ether, amide compounds such as dimethylformamide and dimethylacetamide, or sulfur-containing compounds such as dimethyl sulfoxide. The amount of solvent used is not especially limited either; the raw carboxylic acid can be dissolved under the reaction conditions. As the solvent, a pure product can be used. Alternatively, a solvent recovered from the reaction can be used without any problem.

It is preferable that the amount of urea used in the reaction between a carboxylic acid and urea of the present invention is less than about 0.8 in molar ratio to the carboxylic acid. A more preferable range is about 0.5 to 0.8.

In the reaction between a carboxylic acid and urea of the present invention, the exhaust gas distillate line connected to the reactor refers to the pipe connecting the reactor with a scrubber for catching the exhaust gas, and through the line, the carbon dioxide, water and ammonia byproduct during the reaction, sublimate such as ammonium bicarbonate, decomposition product of urea itself, etc. are discharged. As the material of the pipe, any material can be used without inconvenience if it can resist the compounds discharged.

The heating temperature of the exhaust gas distillate line connected to the reactor should be not lower than about 60° C. which is the sublimation temperature of ammonium bicarbonate mainly contained in the plugging material. A preferable range is about 60 to 250° C., and a more preferable range is about 100 to 220° C. Any heating method can be used without any problem, if the exhaust gas line is kept at about 60° C. or higher.

The reaction between carboxylic acid and urea of the present invention can be effected in the presence of a catalyst such as inorganic acid or cobalt salt. The inorganic acids which can serve as catalysts include boric acid, phosphoric acid, phosphorous acid, sulfuric acid, etc. The cobalt salts which can be used include cobalt borate, cobalt acetate, cobalt oxide, cobalt chloride, cobalt sulfate, etc. One or more or a mixture of these compounds can be used. It is preferable to use cobalt borate or a mixture of boric acid and cobalt acetate. It is preferable that the amount of the catalyst is about 0.01 to 30 wt. % based on the weight of the amide. A more preferable range is about 0.1 to 10 wt. %.

The reaction temperature of the reaction between the carboxylic acid and urea of the present invention depends on the compounds used. It is preferable that the first amidation is effected at about 150 to 350° C. A more preferable range is about 170 to 250° C. It is preferable that the temperature of the subsequent nitrilation is about 200 to 400° C. A more preferable range is about 220 to 300° C.

The reaction can be effected at atmospheric pressure, with pressurization or under reduced pressure. It is preferable that the first amidation is effected at about atmospheric pressure or with pressurization, and that the subsequent nitrilation is effected at about atmospheric pressure or under reduced pressure.

The reaction can be effected in the vapor phase or the liquid phase, but it is preferable that the reaction is effected in the liquid phase. The reaction can be batch or continuous without special inconvenience.

In the present invention, as described before, the reaction between carboxylic acid and urea is also a dehydration of an amide during the stage of nitrilation. Because of the dehydration reaction it is preferable to effect the reaction while removing the produced water. For more advantageous production of a nitrile, as described before, the produced nitrile should be distilled out together with the byproduct water from the reactor during reaction. For this purpose, it is preferable to feed a gas that is inert to the dehydration reaction of the amide. Any gas inactive to the reaction can be used without special restriction, For example, nitrogen, helium, argon or carbon dioxide, etc. can be used. The gas flow rate is required to be about 1 to 300 ml/min per mole of the amide.

The nitrile obtained by the production process can be purified by conventional methods such as distillation or recrystallization, etc. A nitrile can be produced safely at a high yield from the amide dehydration reaction, or from a reaction between urea and carboxylic acid.

The following Examples were conducted by the Applicants or those working under their direction, and correctly indicate the processes performed and the results obtained. They indicate specific ways in which the invention can be practiced, and are not intended to define or to limit the scope of the invention, which is defined in the appended claims outside the scope of the invention.

EXAMPLE 1

A 200 ml four-neck flask equipped with a stirrer, thermometer, gas blow pipe and distillate pipe was charged with 80 g of p-toluamide (0.59 mol; produced by Tokyo Kasei), 20 g of p-toluic acid (0.15 mol; guaranteed reagent, produced by Tokyo Kasei) and 1.60 g of cobalt acetate tetrahydrate (2.0 wt. % based on the weight of p-toluamide; 1st grade reagent, produced by Katayama Kagaku). Reaction was effected at a reaction temperature of 240° C. for 9 hours while nitrogen was blown into the reaction flask at 80 ml/min. After completion of the reaction, the distillate and the residue in the flask were analyzed using high performance liquid chromatography. The p-toluamide conversion percentage was found to be 97.8%. The p-tolunitrile production percentage was 74.4%, and the p-toluic acid byproduction percentage was 13.9%.

EXAMPLE 2

Reaction was effected as described in Example 1, except that 80 g of p-toluamide, 0.32 g of cobalt acetate tetrahydrate and 0.32 g of boric acid were added to 31.3 g of the residue (containing 22.2 g of p-toluic acid, 1.5 g of p-tolunitrile, 1.1 g of p-toluamide and 2.56 g of catalyst) remaining after distilling out p-tolunitrile in Example 1. As a result, the p-toluamide conversion percentage was 94.5%, the p-tolunitrile production percentage was 82.9%, and the p-toluic acid byproduction percentage was 10.6%.

EXAMPLE 3

An exhaust gas distillate pipe was installed in a 200 ml four-neck flask equipped with a stirrer, thermometer, gas blow pipe and distillate pipe. It was heated to 120° C. by a ribbon heater in the range up to a water-filled trap. Into the flask were supplied 100 g of p-toluic acid (0.73 mol; guaranteed reagent, produced by Tokyo Kasei), 2.00 g of cobalt acetate tetrahydrate (1.9 wt. % based on the weight of p-toluamide; guaranteed reagent, produced by Wako Junyaku) and 2.00 g of boric acid (1.9 wt. % based on the weight of p-toluamide; 1st grade reagent, produced by Katayama Kagaku). Reaction was effected at a reaction temperature of 190° C. while 33.15 g of urea (0.55 mol; 0.75 in molar ratio to p-toluic acid) was added, taking 6.75 hours, and furthermore, the reaction mixture was stirred at 190° C. for 1.25 hours. The product was analyzed by high performance liquid chromatography. The p-toluic acid conversion percentage was found to be 85.5 %, p-toluamide production percentage was 79.4% and the p-tolunitrile production percentage was 1.5%. The product was heated to 240° C., and reaction was effected for 9 hours while nitrogen was blown into the reaction flask at 80 ml/min. After completion of reaction, the distillate and the residue in the flask were analyzed by high performance liquid chromatography. The p-toluic acid conversion percentage was found to be 91.5 %, the p-tolunitrile production percentage was 85.2%, and the p-toluamide byproduction percentage was 1.3%.

EXAMPLE 4

Reaction was effected as described in Example 1, except that the nitrogen flow rate was 25 ml/min. As a result, the reaction time was 20 hours, the p-toluamide conversion percentage was 94.5%, the p-tolunitrile production percentage was 82.9%, and the p-toluic acid byproduction percentage was 10.6%.

Comparative Example 1

Reaction was effected as described in Example 1, except that p-toluamide only was supplied in an amount of 100 g, without adding p-toluic acid. As a result, the p-toluamide conversion percentage was 88.7%, the p-tolunitrile production percentage was 57.8%, and the p-toluic acid byproduction percentage was 27.1 %.

Comparative Example 2

Reaction was effected as described in Example 3, except that 100 g of p-toluic acid and 18 g of urea (0.30 mol) were supplied. Reaction was effected with the temperature raised gradually from the melting point of urea, i.e., 130° C. to 190° C. while 40 g of urea (0.67 mol) was added little by little. However, due to sudden reaction halfway, the reaction mixture bumped, and the distillate pipe became plugged. A strong irritating odor of ammonia was generated. Because of these problems, it became almost impossible from a safety viewpoint to effect the reaction, and the reaction was terminated.

Comparative Example 3

Reaction was effected as described in Example 1, except that nitrogen was not fed into the flask. As a result, almost nothing was distilled even after lapse of 7 hours. The reaction was given up. The residue was analyzed, and the p-toluamide conversion percentage was found to be 38.4%, the p-tolunitrile production percentage was 16.7%, and the p-toluic acid byproduction percentage was 22.4%.

What is claimed is:

1. A process for producing a nitrile represented by the following formula (II),

  R—CN    (II)

the steps which comprise:
dehydrating an amide represented by the following formula (I), and:

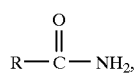    (I)

effecting said dehydration of said amide in the presence of a carboxylic acid represented by the following formula (III):

   R—COOH    (III), where R represents a radical selected from the group consisting of a substituted or non-substituted alkyl group, an alkenyl group, an alkynyl group, an aryl group, and an aralkyl group and mixtures thereof.

2. A process according to claim 1, wherein said dehydration of said amide is effected in the presence of a residue from incomplete conversion of said carboxylic acid, said remaining after producing residual nitrile represented by said formula (II).

3. A process as defined in claim 2, characterized in that the conversion percentage of said carboxylic acid is less than about 100%, and that said dehydration reaction is effected while carboxylic acid represented by said formula (III) remains together with produced amide.

4. A process according to claim 1, wherein urea is added to the carboxylic acid represented by said formula (III) when the carboxylic acid is in a molten condition.

5. A process according to claim 3, wherein urea is added to the carboxylic acid represented by said formula (III) when said carboxylic acid is dissolved in a solvent.

6. A process according to claim 3, wherein the amount of urea used is less than about 0.8, expressed as molar ratio to said carboxylic acid.

7. A process according to claim 1, wherein said radical R of formula (I) comprises a substituted or non-substituted aryl group having about 6 to 20 carbon atoms.

8. A process according to claim 1, wherein the amide represented by said formula (I) is an amide represented by the following formula (IV):

where R' represents an alkyl group having 1 to 4 carbon atoms, an alkoxy group having 1 to 4 carbon atoms or halogen atom, and where n represents the number 0, 1 or 2.

9. A process according to claim 1, wherein a gas that is inert to the dehydration reaction of said amide is introduced during said reaction, and wherein said produced nitrile and water are distilled out during said introduction.

10. A process according to claim 9, wherein said inert gas is selected from the group consisting of nitrogen, helium, argon and carbon dioxide.

11. A process according to claim 1, wherein the R radicals in said compounds (I), (II) and (III) are aryl groups.

12. A process according to claim 1, wherein an inorganic acid and/or a cobalt salt is introduced as a catalyst in said reaction.

13. A process according to claim 1, wherein an exhaust gas distillate line is connected to a reactor for discharging the byproducts of said reaction, and wherein said distillate line is maintained at a temperature of about 60° C. or higher.

* * * * *

UNITED STATES PATENT AND TRADEMARK OFFICE
CERTIFICATE OF CORRECTION

PATENT NO. : 5,965,764
DATED : October 12, 1999
INVENTOR(S) : Matsuoka et al

It is certified that error appears in the above-identified patent and that said Letters Patent is hereby corrected as shown below:

On the Title Page at [56], please add 5,550,286 8/27/96 Christidis et al.-- ; after the Abstract, please change "13 Claims" to -- 14 Claims-- .

In Column 1, at approximately line 30, please change "nitrites" to -- nitriles-- .

Column 4, line 29, change "$R^1$" to -- $Rn^1$-- .

UNITED STATES PATENT AND TRADEMARK OFFICE
CERTIFICATE OF CORRECTION

PATENT NO. : 5,965,764
DATED : October 12, 1999
INVENTOR(S) : Matsuoka et al.

It is certified that error appears in the above-identified patent and that said Letters Patent is hereby corrected as shown below:

Column 4, lines 20-28, please remove the formula and substitute the following:

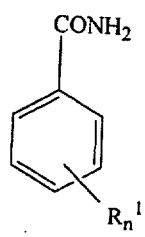

Claim 8, which appears on column 10, lines 30-35, please remove the formula and substitute the following:

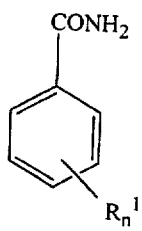

UNITED STATES PATENT AND TRADEMARK OFFICE
CERTIFICATE OF CORRECTION

PATENT NO. : 5,965,764
DATED : October 12, 1999
INVENTOR(S) : Matsuoka et al

It is certified that error appears in the above-identified patent and that said Letters Patent is hereby corrected as shown below:

In Column 10, on line 2, after "amide" please insert -- represented by formula (I)-- and before "residue" please insert -- carboxylic acid -- ;

line 3, please delete "from incomplete conversion of said carboxylic acid, said";

line 4 please delete "residual" and insert -- the-- ;

line 7 to 11 please delete "as defined in claim 2, characterized in that the conversion percentage of said carboxylic acid is less than about 100%, and that said dehydration reaction is effected while carboxylic acid represented by said formula (III) remains together with produced amide." and insert -- for producing a nitrile, in which an amide represented by the following formula (I):

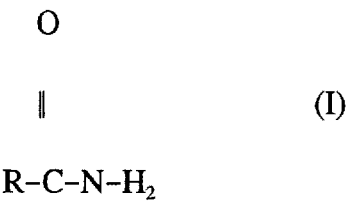

group, aryl group or aralkyl group) is obtained by the reaction between a carboxylic

UNITED STATES PATENT AND TRADEMARK OFFICE
CERTIFICATE OF CORRECTION

PATENT NO. : 5,965,764
DATED : October 12, 1999
INVENTOR(S) : Matsuoka et al

It is certified that error appears in the above-identified patent and that said Letters Patent is hereby corrected as shown below:

acid represented by the following formula (III):

$$R\text{-}COOH \qquad (III)$$

(where R stands for a substituted or non-substituted alkyl group, alkenyl group, alkynyl group, aryl group or aralkyl group) and urea, and subsequently a nitrile represented by the following formula (II):

$$R\text{-}CN \qquad (II)$$

(where R stands for a substituted or non-substituted alkyl group, alkenyl group, alkynyl group, aryl group or aralkyl group) is produced by the dehydration reaction of the amide represented by the formula (I), characterized in that the conversation percentage of the carboxylic acid represented by said formula (III) is less than 100% and that the dehydration reaction is effected while the carboxylic acid represented by said formula (III) remains in the produced amide.--

UNITED STATES PATENT AND TRADEMARK OFFICE
CERTIFICATE OF CORRECTION

PATENT NO. : 5,965,764
DATED : October 12, 1999
INVENTOR(S) : Matsuoka et al

It is certified that error appears in the above-identified patent and that said Letters Patent is hereby corrected as shown below:

In column 10, on line 13, please change "claim 1" to -- claim 3-- ;

line 21 please change "claim 3" to -- claim 4--;

line 25 please change "claim 1" to -- claims 1 or 3,-- ;

at approximately line 29 please change "claim 1" to -- claims 1 or 3,-- ; and please substitute the following formula (IV) for the formula of record:

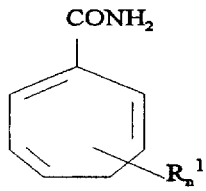

On line 43, please change "$R^1$" to -- $Rn^1$-- .

On approximately line 46, please change "claim 1," to --claims 1 or 3,--.

UNITED STATES PATENT AND TRADEMARK OFFICE
CERTIFICATE OF CORRECTION

PATENT NO. : 5,965,764
DATED : October 12, 1999
INVENTOR(S) : Matsuoka et al

It is certified that error appears in the above-identified patent and that said Letters Patent is hereby corrected as shown below:

On approximately line 55, line 1, please change "claim 1," to --claims 1 or 3,--.

On approximately line 58, please change "claim 1," to --claims 1 or 3,--.

On approximately line 62, please change "claim 1," to --claims 1 or 3,--.

Please add new Claim 14 as follows:

-- Claim 14. A process according to claim 5, wherein the amount of urea used is less than about 0.8, expressed as molar ratio to said carboxylic acid.--

Signed and Sealed this

Twelfth Day of December, 2000

Attest:

Q. TODD DICKINSON

*Attesting Officer*    *Director of Patents and Trademarks*